United States Patent [19]

Ayer et al.

[11] 4,285,987
[45] Aug. 25, 1981

[54] PROCESS FOR MANUFACTURING DEVICE WITH DISPERSION ZONE

[75] Inventors: Atul D. Ayer, Mountain View; Felix Theeuwes, Los Altos, both of Calif.

[73] Assignee: Alza Corporation, Palo Alto, Calif.

[21] Appl. No.: 90,492

[22] Filed: Nov. 1, 1979

Related U.S. Application Data

[63] Continuation of Ser. No. 953,906, Oct. 23, 1978, Pat. No. 4,200,098.

[51] Int. Cl.³ .............................................. A61M 7/00
[52] U.S. Cl. ....................................................... 427/3
[58] Field of Search ......................... 427/3; 424/19, 2; 128/260

[56] References Cited

U.S. PATENT DOCUMENTS 3,961,628 6/1976 Arnold ................................... 424/21
4,200,098 4/1980 Ayers ................................... 428/420

Primary Examiner—Sam Silverberg
Attorney, Agent, or Firm—Paul L. Sabatine; Edward L. Mandell

[57] ABSTRACT

An osmotic system is disclosed for dispensing a beneficial agent. The system comprises (1) a first wall of a semipermeable material that surrounds a compartment containing a drug formulation, and has a passageway through the wall for releasing agent from the compartment, (2) a second wall positioned distant from the first wall, said second wall a microporous or hydrogel material that extends around the first wall, and (3) a distribution zone interposed between the first and second wall and initially housing a compound soluble in an external fluid that enters the system.

In operation, agent is dispensed from the system by fluid passing through the second wall into the zone from which fluid is further being imbibed through the first wall into the compartment forming a solution that is released through the passageway into the zone, and then through the second wall to the exterior of the system.

15 Claims, 14 Drawing Figures

PROCESS FOR MANUFACTURING DEVICE WITH DISPERSION ZONE

REFERENCE TO RELATED APPLICATION

This application is a continuation of U.S. patent application Ser. No. 953,906 filed on Oct. 23, 1978, now U.S. Pat. No. 4,200,098.

FIELD OF THE INVENTION

This invention pertains to a novel and useful osmotic system for the controlled delivery of a beneficial agent to an environment of use. More particularly, the invention relates to an osmotic system comprising an agent distribution zone for aiding in controlling the spatial delivery profile, the concentration of agent delivered from the system over a prolonged period of time, and the physical rigidity of the system.

BACKGROUND OF THE INVENTION

Osmotic systems for delivering a beneficial agent to an environment of use are known to the art in U.S. Pat. Nos. 3,854,770 and 3,916,899. The osmotic systems disclosed in these patents are made with a semipermeable wall that surrounds a compartment containing agent. The semipermeable wall is permeable to an external fluid and substantially impermeable to agent. The system has a passageway through the semipermeable wall for delivering agent from the compartment to the environment of use. These systems are extraordinarily effective for delivering an agent that is soluble in fluid that enters the compartment and exhibit an osmotic pressure gradient across the semipermeable wall against the fluid, and also for delivering an agent that has limited solubility in the fluid. In this latter embodiment, the agent is mixed with an osmotically effective compound that is soluble in the fluid and exhibits an osmotic pressure gradient across the semipermeable wall against the fluid.

These prior art osmotic systems release their agent by imbibing fluid through the semipermeable wall into the compartment at a rate determined by the permeability of the semipermeable wall and the osmotic pressure gradient across the semipermeable wall producing a solution of soluble agent, or a solution of soluble compound containing agent, which solution in either operations is dispensed at a controlled rate through the passageway to the exterior of the device over a prolonged period of time.

The prior art described above represents an outstanding and pioneering advancement in the delivery art. The osmotic systems are useful for dispensing beneficial agents to the environment of use. Now, it has been found, these osmotic systems can have novel, inventive improvements that enhance the usefulness of the systems and broaden their application. For example, osmotic systems made according to the invention have an agent distribution zone and a second wall. These act together as a single entity, and they dispense an agent released from the system over a broader receptive area per unit of time. That is, they produce an agent distribution profile in both time and space. It will be appreciated by those versed in the art, these improvements represent a substantial contribution to the delivery art. For example, the present systems can dispense an agent over a wider area than is possible with a single passageway system, and they can decrease the amount of agent presented to a receptor site. Accordingly, the systems of this invention can be advantageously used for lessening the possible incidence of unwanted agent-receptor interreaction. It will, therefore, be appreciated the osmotic systems of this invention have a positive value in the medical and veterinary arts. In addition, the properties of the second wall can be selected such that the rigidity of the system can be programmed.

OBJECTS OF THE INVENTION

Accordingly, it is an immediate object of this invention to provide an osmotic system for the controlled delivery of an active agent over a prolonged period of time, which system is an improvement over the systems known to the prior art.

Another object of the invention is to provide an osmotic system that can produce an agent distribution profile in time and space, and can dilute and disperse the agent over an increased agent receptor site.

Yet another object of the invention is to provide a solid dosage osmotic system, which system in actual operation has a softness to touch produced by a liquid cushion in the system.

Still another object of the invention is to provide an osmotic delivery system manufactured in the form of an osmotic drug delivery device that provides a drug delivery profile that can be controlled in space, while in the past it could be controlled only in time.

Yet still another object of the invention is to provide an osmotic system for delivering a drug, which system in operation feels as a semisolid drug dosage form and delivers the drug in spacial distribution and dilution over a prolonged period of time.

Other objects, features and advantages of this invention will be more apparent to those skilled in the art from the following detailed specification, taken in conjunction with the drawings and the accompanying claims.

STATEMENT OF THE INVENTION

This invention concerns an osmotic system for dispensing a beneficial and useful agent. The system comprises a semipermeable or inner wall that surrounds a compartment housing an agent with a passageway through the semipermeable wall for releasing agent from the compartment. The system also has a microporous or hydrogel wall, that is an outer wall positioned distant from and extended around the semipermeable wall. The system has a spatial zone between the inner and outer walls that extends around the area between the inner and outer wall and houses a fluid soluble compound.

In operation, agent is dispensed from the system by (a) external fluid passing through the outer wall into the zone forming a solution containing the compound that is released through the outer wall to the exterior or the system, by (b) fluid being imbibed from the zone through the inner wall into the compartment forming a solution of formulation that is released through the passageway into the zone, with (c) said formulation continuously filling the zone and passing from the zone through the outer wall to the exterior of the system to provide an agent distribution in space and time.

BRIEF DESCRIPTION OF THE DRAWINGS

In the drawings, which are not shown to scale, but are set forth to illustrate various embodiments of the invention, the figures are as follows.

In the drawings and specification, like parts in related figures are identified by like numbers. The terms appearing earlier in the specification and in description of the drawings, as well as embodiments thereof, are further detailed elsewhere in the disclosure.

DETAILED DESCRIPTION OF THE DRAWINGS

Figure 1:
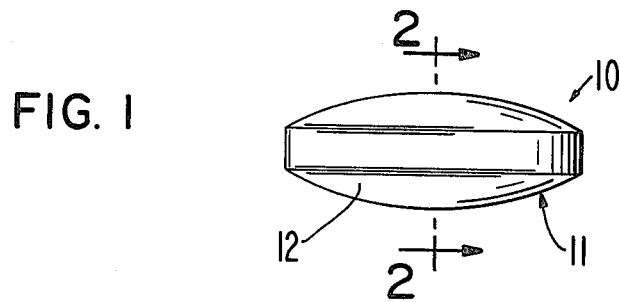
FIG. 1 is a view of an osmotic system manufactured in the form of an osmotic device designed for orally delivering a beneficial agent.

Turning now to the drawings in detail, which are examples of various osmotic delivery systems of the invention, and which examples are not to be considered as limiting, one example of an osmotic system is indicated by the numeral 10. System 10, as seen in FIG. 1, comprises a body 11 having a wall 12. Wall 12, is an outer positioned wall, and it is formed of a member selected from the group consisting of a microporous and hydrogel material, a description of which is presented later in this specification. System 10, of FIG. 1, is manufactured as an osmotic oral device, sized, shaped and adapted for dispensing a drug to the gastrointestinal tract.

Figure 2:
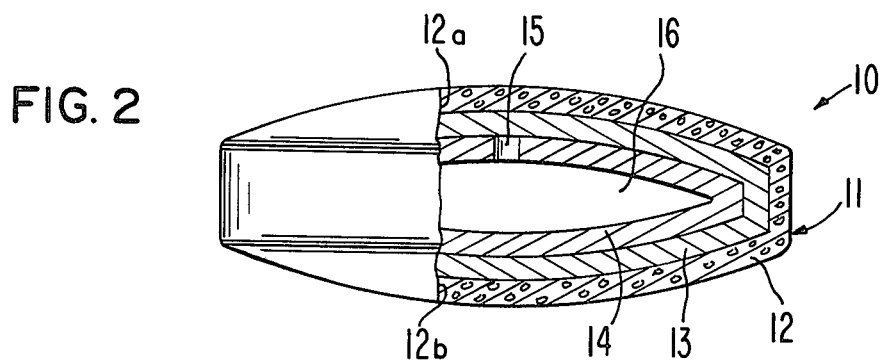
FIG. 2 is a view of the osmotic system of FIG. 1 in opened section for illustrating the structure of the system.

FIG. 2 depicts the osmotic system of FIG. 1 in opened section at 2—2 of FIG. 1. In FIG. 2, a section of outer wall 12 is removed from 12a to 12b for illustrating the structure of osmotic system 10. System 10, as seen in FIG. 2, comprises (1) a first wall 14, also identifiable as an inside wall, which wall 14 is formed of a semipermeable material that is permeable to the passage of fluid and substantially impermeable to the passage of agent, drug and osmotically effective compounds. Semipermeable wall 14 surrounds, forms and defines a compartment 16, and there is a passageway 15 through semipermeable wall 14 for releasing an agent from compartment 16. System 10 also comprises (2) a second wall 12, positioned distant in spaced relation from first wall 14. Wall 12 is an outer wall, and wall 12 is formed of a member selected from the group consisting of a microporous and hydrogel materials. Wall 12 extends around wall 14 with walls 12 and 14 defining a distribution zone 13, or space between walls 12 and 14. Zone 13 initially is filled with a layer of a compound that is soluble in fluid present in the environment of use which enters system 10.

Figure 3:
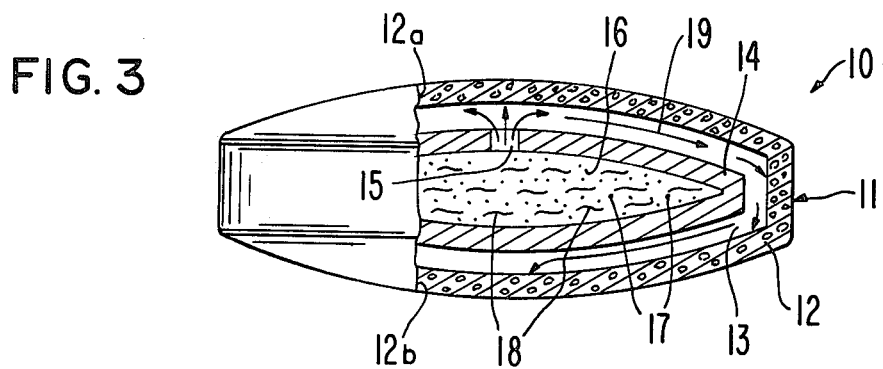
FIG. 3 is a view of the osmotic system of FIG. 1 in opened section as in FIG. 2 for illustrating the mode of operation of the system.

FIG. 3 is a continuation of FIG. 2, depicting FIG. 2 in operation dispensing an agent formulation 17, represented by dots, to the environment of use. In operation, agent 17 is dispensed from system 10 by external fluid passing through wall 12 into zone 13, while agent present in zone 13 diffuses through wall 12. Fluid now present in zone 13, then is imbibed through wall 14 into compartment 16 forming a solution 18, represented by wavy lines, containing agent 17. Solution 18 is released through passageway 15 into zone 13 continuously filling zone 13, for both distribution through zone 13 from which agent diffuses to the exterior of system 10. The distribution of agent 17 in zone 13 is indicated by flow lines 19 having directional arrows. The release of agent 17 from total distribution zone 13 through wall 12 dispenses agent 17 around the exterior of system 10 producing an agent distribution in space and time in the environment of use. The presence of fluid in zone 13 also imparts a softness to system 10. This feature increases the usefulness of system 10 for dispensing agent 17 in animal opening, such as the anal and vaginal canals, presented hereafter.

Figure 4:
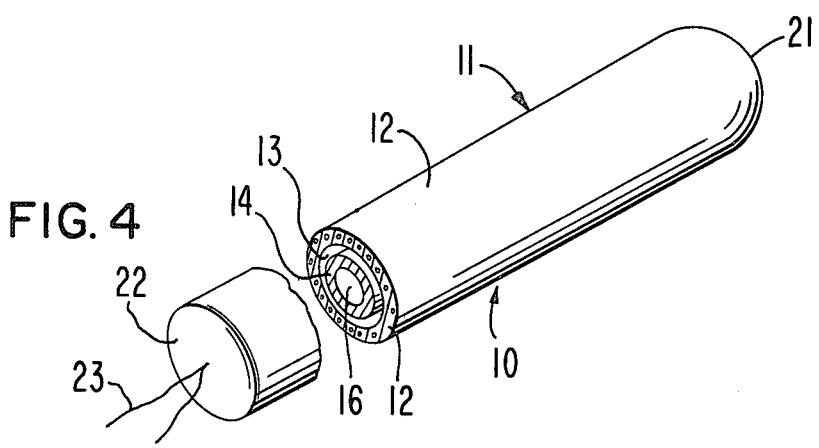
FIG. 4 is a perspective view of another embodiment of the invention comprising an osmotic system shaped, sized and adapted for dispensing a drug in the anal or vaginal canals.
Figure 5:
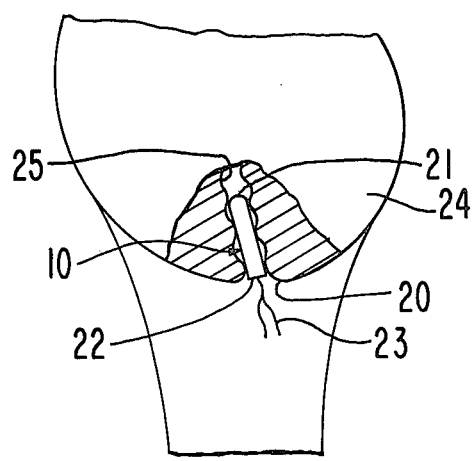
FIG. 5 shows the osmotic system of FIG. 4 dispensing drug in the anal-rectal canal.

FIG. 4 illustrates osmotic system 10 designed for releasing an agent within an animal body opening, the anal canal, as seen in FIG. 5 and identified by the number 20. In FIG. 4, system 10 is seen comprising a tubular body 11 having a rounded, tapered front end 21, a rear end 22 and a string 23. System 10 is illustrated in opened section for viewing the components of system 10, which consists essentially of semipermeable wall 14, compartment 16, distribution zone 13 and outside wall 12. The components of system 10 not seen in FIG. 4 are seen in FIG. 3, presented above.

Referring now to the drawings, FIG. 5 shows a body 24 having an anal canal 25 located between the buttocks. Anal canal 25 terminates in an anus 20, and it has the usual Crypts of Morgagni residing in the rectal ampulla. A spincter muscle surrounds anus 20. The anatomical features not delineated in FIG. 5 are known in *Anatomy of the Human Body*, by Gray, H., 1954, published by Lea and Febiger, Philadelphia, Pa. System 10 has the relatively soft features discussed above, and those features make it possible for system 10 to reside snugly and comfortably in anal canal 25.

The osmotic therapeutic system illustrated in FIGS. 4 and 5 makes many advantages available to the anal-rectal dispensing art that represent a significant improvement over the prior art suppositories. For example, osmotic system 10 will not leak from the body orifice into which it is inserted. This is of significant value in the administration and application of medicaments. The prior art suppositories, usually made of oleaginous base materials, although widely used for delivery of medication, have several glaring faults that detract from their usefulness. The suppositories melt or dissolve in body fluids upon insertion into the body orifice and the formed liquid oftentimes flows from the body orifice. This initial leakage may occur before the medication to be administered has sufficient time to be absorbed and produce the desired effect. The leakage also is undesirable from an esthetic and therapeutic consideration, for besides the spoiling of garments, the continual leakage carries with it unknown amounts of medicine from the body. The present osmotic system substantially eliminates these prior art problems. Additionally, the present systems are non-irritating to the body as they are made of materials that are essentially free of interaction between the system and the mucosal surface of the body canal.

Figure 6:
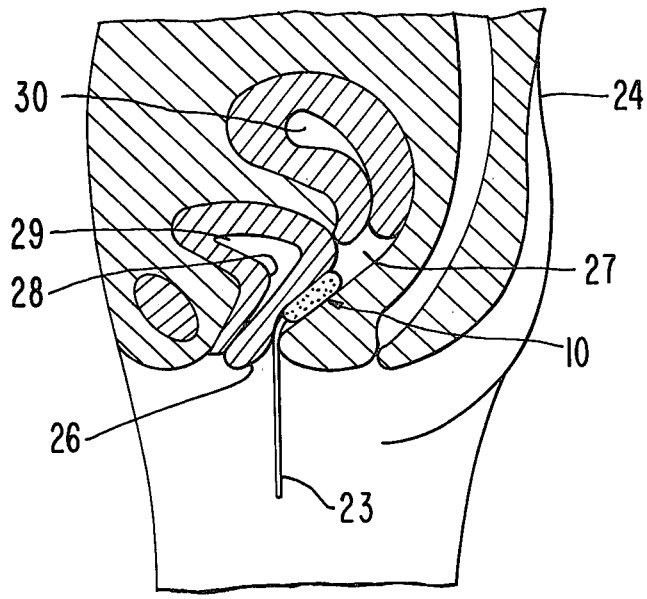
FIG. 6 shows the osmotic system of FIG. 4 dispensing drug in the vaginal canal.

Referring now to the drawing, FIG. 6 shows another osmotic dispensing system 10 made according to the mode and the manner of the invention. FIG. 6 additionally shows a body 24 having a vaginal entrance 26 leading to vaginal canal 27 that provides access to reproductive uterus 30. Body 24 also has a bladder 29 with an exit through urinary canal 28. An osmotic vaginal dispensing system 10, sized, shaped and adapted for insertion is seen in vaginal canal 27. System 10 is made and structured as described supra, and system 10 operates in a like manner. System 10 has a string 23 for manually removing system 10 from the biological environment of use.

Vaginal system 10 is made from non-erodible, biologically inert, vaginally acceptable materials that maintain their physical and chemical integrity at body temperatures. System 10 additionally is designed to (a) avoid inadvertent over-application of medication when dispensing same, to (b) absorb the effects of vaginal motion and pressure through fluid distribution zone 13 for comfortable retention of system 10 in vaginal canal 27, to (c) provide a unit, dosage amount in either liquid or semiviscous form for completing the desired therapeutic program, and to (d) dispense and disperse released drug around the perimeter of system 10 thereby providing a drug distribution profile in space and time.

Figure 7:
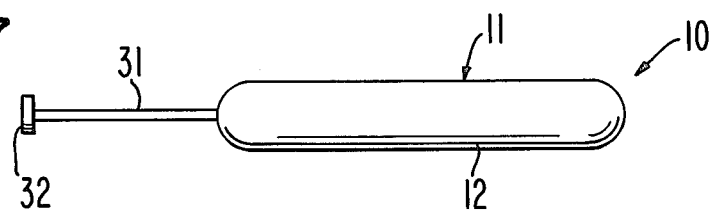
FIG. 7 illustrates an osmotic system made according to the invention designed for use as an implant.

FIG. 7 illustrates another embodiment of the present invention. FIG. 7 depicts osmotic system 10 sized, shaped and adapted as an implant. System 10 of FIG. 7 has the added feature of a connecting member 31 that joins body 11 with a restraining member 32 for keeping system 10 anchored into the tissues of a living organism. Connecting member 31 is preferably a non-erodible polymeric string and restraining member 32 is made of a similar material.

While FIGS. 1 through 7 are illustrative of various osmotic systems that can be made according to the invention, it is to be understood these systems are not to be construed as limiting, as the systems can take a wide variety of shapes, sizes and forms for delivering agent formulation to different environments of use. For example, the systems also include buccal, artificial gland, cervical, intrauterine, ocular and ear systems. The systems also can be adapted for delivering an active agent in streams, aquariums, fields, factories, reservoirs, laboratory facilities, hot houses, transportation means, plant farms, naval means, air and military means, hospitals, veterinary clinics, nursing homes, chemical reactants, and other environments of use.

DETAILED DESCRIPTION OF THE INVENTION

In accordance with the practice of this invention, osmotic dispensing system 10, in one presently preferred embodiment has improved properties, which are characterized by microporous wall 12 and distribution zone 13, as illustrated in FIGS. 2 and 3. For an osmotic system 10 as shown in FIG. 2, the rate of release is given by equation (1):

$$(dm/dt)_t = (\pi_s \cdot S)/R_t \qquad (1)$$

wherein $\pi_s$ is the osmotic pressure of saturated drug solution 17 in reservoir 16, S is the solubility of the drug formulation in fluid in reservoir 16, and $R_t$ is the total resistance to water transport of microporous wall 12 or $R_3$, layer 13 or $R_2$ and semipermeable wall 14 or $R_1$. The total resistance to water transport is given by equation (2):

$$R_t = R_1 + R_2 + R_3 \qquad (2)$$

The resistance of $R_2$ is usually small and it can be combined with the resistance of $R_3$, the microporous wall.

In the absence of $R_2$ and $R_3$, osmotic system 10 resembles an elementary osmotic pump with a delivery rate given by equation (3):

$$(dm/dt)_1 = K_1(A_1/h_1) \cdot \pi_s \cdot S \qquad (3)$$

wherein $K_1$ is the permeability of semipermeable wall 14 having an area $A_1$ and a thickness $h_1$. The drug's osmotic pressure is $\pi_s$ and its solubility S. Thus, equation (3) can be presented as equation (4) as follows:

$$(dm/dt)_1 = (\pi_s \cdot S)/R_1 \qquad (4)$$

with $R_1$ defined by equation (5):

$$R_1 = h_1/(K_1 \cdot A_1) \qquad (5)$$

Therefore, from equations (1) and (5) it follows the ratio of the release rates for an osmotic system made with only semipermeable wall 14 or 1, to an osmotic system made with microporous wall 12, distribution layer 13 and semipermeable wall 14 is given by equation (6):

$$\frac{(dm/dt)_1}{(dm/dt)_t} = 1 + \frac{R_3}{R_1} \qquad (6)$$

The resistance of microporous wall 12 in combination with distribution zone 13 is then measured by plotting the ratio of $(dm/dt)_1/(dm/dt)_t$ as a function of $1/R_2$ with the increase in the resistance of semipermeable wall 14 calculated from equations (4) and (5).

The programming of the hydrostatic pressure within distribution zone 13 is a novel and important embodiment for systems made according to this invention. The embodiment is important because the rigidity of an osmotic system now can be programmed for enhancing the usefulness of the system. That is, system 10 rigidity is governed by the hydrostatic pressure generated within distribution zone 13. For example, when the hydrostatic pressure in zone 13 is low and close to the pressure outside system 10, system 10 feels soft and can be deformed easily. Also, when the pressure in zone 13 is larger than the pressure outside system 10, the system feels hard, much like a football under pressure. A characteristic of this system is that the pressure difference between zone 13 and the outside can be programmed to determine the degree of softness of the system.

It is known from studies in reverse osmosis, that at a condition of zero fluid net flow across a membrane, which is the condition generated in this system at a steady state operation, that the hydrostatic pressure generated across wall 12 is given by equation (7):

$$\Delta P = \sigma \Delta \pi \qquad (7)$$

wherein is the microporous wall's reflection coefficient, and in terms of osmotic system 10, the operating parameters of equation (7) can be expressed by equation (8) as follows:

$$P_2 - P_e = \sigma_3 \cdot (\pi_2 - \pi_e) \tag{8}$$

wherein $P_2$ and $P_e$ are the hydrostatic pressure in distribution zone 13, or $P_2$, and the environment, or $P_e$, and $\pi_e$ are respectively the osmotic pressures. Thus, for equation (8), it follows the rigidity of system 10 can be expressed by $P_2 - P_e$ and be programmed by the osmotic pressure difference and the reflection coefficient $\sigma_3$ of microporous wall 12. Thus, when microporous wall 12 permits the passage of fluid, system 10 will feel soft, and when wall 12 is in a compound or salt rejecting state, system 10 will feel rigid. The additional surface characteristics of system 10 can be preselected by governing the selection of wall forming polymers possessing hydrophilic versus hydrophobic properties. For example, by using a hydroxyethyl methacrylate/hydroxymethyl methacrylate block copolymer, both the surface characteristics and the reflection coefficient of wall 12 can be selected to give a particular feel. The osmotic pressure $\pi_2$ is calculated from the average drug concentration $C_2$ within distribution zone 13 as derived from equation (9), Van T'Hoff's Law:

$$\pi_2 = C_2(\pi_s/S) \tag{9}$$

with the average concentration $C_2$ can further be obtained from system 10 total delivery rate by equation (10):

$$C_2 = (1/P_3) \cdot (h_3/A_3) \cdot (dm/dt)_t \tag{10}$$

wherein $P_3$ is the permeability of the microporous wall to drug, and $A_3$ and $h_3$ are the area and thickness of said wall. The permeability constant $P_3$ of said wall is determined by permeation experiments. In this permeation experiment $P_3$ and $\sigma_3$ can be determined simultaneously by methods disclosed in Transport Phenomena in Membranes, by N. Lakshminarayanania, 1969, published by Academic Press.

Although $P_3$ and $\sigma_3$ are related, and cannot be varied totally independently of each other, it is possible to select a delivery rate $(dm/dt)_t$ for the total system independent of its rigidity; since, the delivery rate from the system is determined by the characteristics of wall 12 and 14. The rigidity can be programmed by the reflection coefficient of agent $\sigma_3$ of outside wall 12. Values of $\sigma_3$ between 0 and 1 are programmed by the porosity of wall 12 as effected by the (a) degree of hydrophobicity of wall 12, and (b) the degree of loading of pore-formers in wall 12. Substantially soft systems can be obtained by selecting (a) wall forming polymers with water sorption in the range of 60 to 90%, and (b) loading pore-former agents in wall 12 in the range of 60 to 90%. Substantially more rigid systems can be programmed for systems having a wall 12 with water sorption in the range of 30 to 60% and pore formers in the same content range.

The programming of the degree of beneficial agent dispersion from the present osmotic system is another novel and useful embodiment of this invention. The spatial distribution of drug delivery in the environment of use enhances the delivery properties of system 10 over an osmotic system having a single delivery orifice, or a limited number of orifices. For example, in certain pharmaceutical or other applications, it is desirable that the spatial pattern of agent distribution should be diffused. Application of this kind include when a tissue site should be treated in its entirety where a high local concentration should be avoided, or where the agent should be dispersed to increase absorption. In contrast to the extreme application of a system that disperses an agent in a uniform fashion, are systems where an agent is delivered through a homogeneous membrane. The system of this invention can be used to achieve any intermediate spatial delivery pattern.

In the present system, a localized flux around the portion of the orifice is obtained when the resistance of the microporous wall is small compared to the resistance of the semipermeable membrane $(R_3 < R_1)$, when the resistance of $R_3$ becomes equal to $R_1$, the delivery rate profile is distributed over the total surface area. When $R_3$ is much larger than $R_1$, the delivery rate profile tends to be uniform over the whole wall surface area.

Further, in accordance with the spirit of the invention, osmotic dispensing system 10 is manufactured with a first wall 14 formed of a semipermeable material. The semipermeable materials are permeable to the passage of fluids including water and biological fluids, and they are substantially impermeable to the passage of agents, drugs, compounds and solutes. The semipermeable materials include semipermeable homopolymers and semipermeable copolymers. In one embodiment, the semipermeable materials generically include polysaccharides comprising anhydroglucose units. The polysaccharides are cellulose esters and ethers having a degree of substitution, D.S., on the anhydroglucose unit from greater than 0 up to 3 inclusive. By "degree of substitution" as used herein is meant the average number of hydroxyl groups on the anhydroxyl groups of the anhydroglucose unit of the polymer that is replaced by a substituting group. An exemplary semipermeable polymeric material is represented by the following formula:

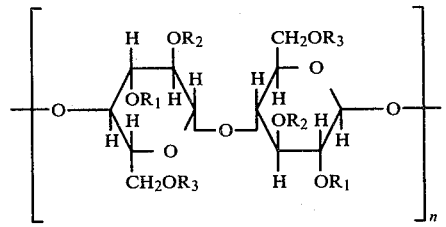

wherein $R_1$, $R_2$ and $R_3$ are the same or different and they are a member selected from the group consisting essentially of hydrogen; alkyl; alkenyl; amino; acyl; acyl substituted with a member selected from the group consisting of alkoxy, halogen, hydroxyl, alkanoyl, carboalkyl, carboalkoxy, and cyanoalkoxy; aroyl; aroyl substituted with a member selected from the group consisting of hydroxyl, carboxyl, carboalkyl and cyano; aryl; benzyl; phenyl; carboalkyl; carboalkyl; dialkoxyalkyl; dithiocarbonyl; hydroxyalkyl; cyanoalkyl; nitro; sulfoalkyl; trityl; carbamoyloxyalkyl; carboxyalkoxyacyl; carboxybenzoyl; carboxybenzoyloxyalkyl; dialkylaminohydroxyalkyl; the alkali metal salts thereof; n is greater than 5, usually 10 to $3 \times 10^6$; and wherein the polymer exhibits a degree of substitution at $R_1$, $R_2$ and $R_3$ of greater than 0 up to 3.

Exemplary alkyl groups for the purpose of the invention are the straight and branched chain type having 1 to 20 carbons, such as methyl, ethyl, n-propyl, iso-propyl, n-butyl, sec-butyl, pentyl, neo-pentyl, n-hexyl, isohexyl, heptyl, 4,4-dimethyl pentyl; 2,2,4-trimethylpentyl, nonyl, decyl, 2,5-dimethyl decyl, and the like. By "alkenyl" is meant straight or branched chain alkenyl groups of 2 to 20 carbons such as 1-propenyl, 2-propenyl or alkyl, 1-butenyl, 2-butenyl, 1-pentyl, and the corresponding positional isomers such as 1-isobutenyl, 2-isobutenyl, 2-sec-butenyl, 2-methyl-1-butenyl, 2-methyl-2-pentylnyl, 2,3-dimethyl-3-hexenyl, and the like. The term "alkoxy" as used herein includes the straight and branched chain alkoxy groups having 1 to 20 carbons inclusive; for example, methoxy, ethoxy, propoxy, butoxy, n-pentoxy, n-hexoxy, iso-propoxy, 2-butoxy, isobutoxy, 3-pentoxy, n-octoxy, and the positional isomers thereof.

The term acyl as used herein includes moieties such as alkanoyl and alkenoyl. Typical alkanoyls have 1 to 20 carbon atoms such as formyl, acetyl, propionyl, butyrl, hexanoyl, heptanoyl, octanoyl, undecanoyl, lauroyl, palmitoyl, stearoyl, oleoyl, and isomeric forms thereof. The term aroyl as used herein includes aroyls of 7 to 15 carbon atoms such as benzoyl, phenylacetyl, cinnamoyl, naphthoyl, p-ethoxybenzoyl, alloxyphenylacetyl, p-nitrobenzoyl, 3-chlorobenzoyl, and the like.

Exemplary aryls include 6 to 15 carbons such as phenyl, benzyl, naphthyl, and the like. Exemplary halogens include fluorine, bromine and chlorine. Representative alkali metal salts include sodium, potassium, lithium, and the like. Exemplary hydroxyalkyl include hydroxyalkyl having an alkyl of 1 to 20 carbons such as hydroxymethyl, hydroxyethyl, hydroxypropyl, hydroxybutyl, hydroxyhexyl, and the like.

Representative semipermeable polymers suitable for forming wall 14 include cellulose esters and cellulose ethers such as cellulose acylate, cellulose diacylate and cellulose triacylate. Exemplary semipermeable polymers include cellulose acetate having a D. S. up to 1 and an acetyl content up to 21%; cellulose diacetate having a D.S. of 1 to 2 and an acetyl content of 21 to 35%; cellulose triacetate having a D.S. of 2 to 3 and an acetyl content of 35 to 44.5%; cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%, an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a degree of substitution prepared by the hydrolysis of the corresponding triester to yield cellulose diacylates having a D.S. of 2.2 to 2.6 such as cellulose disuccinate, cellulose dipalmitate, cellulose dioctanoate, cellulose dicaprylate, and cellulose dipentanate; and esters prepared from acyl anhydrides or acyl acids in an esterification reaction to yield esters containing different acyl groups attached to the same cellulose polymer, such as cellulose acetate valerate, cellulose acetate succinate, cellulose propionate succinate, cellulose acetate octanoate, cellulose valerate palmitate, cellulose acetate palmitate, and cellulose acetate heptanoate.

Additional semipermeable polymers include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, methyl cellulose acetate, methylcyanoethyl cellulose, cellulose acetate methoxyacetate, cellulose acetate, cellulose acetate ethoxyacetate, cellulose acetate dimethylsulfamate, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methyl carbamate, acylated polysaccharides, acylated starches, sulfomethyl cellulose, aminocellulose acetate, cellulose acetate diethylamino acetate, semipermeable walls made from polymeric epoxides, copolymers of alkylene oxides and alkyl glycidyl ethers, semipermeable polyurethanes, cellulose acetate carboxymethoxypropionate, cellulose acetate phthalate, cellulose butyrate naphthylate, methylcellulose acetate, cellulose acetate methylcarbamate, tritylcellulose hydroxypropyl methylcellulose phthalate, hydroxypropylbutyl cellulose phthalate, hydroxyethylcellulose, hydroxypropylcellulose, hydroxybutyl methylcellulose, benzyl cellulose, sodium carboxymethylcellulose, sodium carboxymethylhydroxyethyl cellulose, carbamoylethyl cellulose, carboxyethylcellulose, 2-carboxybenzoyloxy propylcellulose, and the like.

Generally, the semipermeable polymers useful for forming wall 14 will have a fluid permeability of $10^{-5}$ to $10^{-1}$ (cc.mil/cm$^2$.hr.atm), expressed per atmosphere (atm) of hydrostatic or osmotic pressure difference across the membrane at the temperature of use while possessing impermeability to agents, drugs and solutes are useful for the purpose of the invention. The polymers described above are known to the art in references such as Chemical Abstracts, Vol. 44, 8675 (g), 1956; ibid., 50, 11248 (e), 1957; ibid., 51, 10892(c), 12463 (f), 1957; ibid., 55, 10888(a), 17002(h), 1961; and ibid., 12024(m), 12026(p), 1967; in U.S. Pat. Nos. 3,646,179; 3,718,728; 3,721,582; 3,732,205; 3,896,108; and 3,892,665; or they can be prepared according to the procedures in *Encyclopedia of Polymer Science and Technology*, Vol. 3, pages 325 to 354, and 459 to 549, 1964, published by Interscience Publishers, Inc., New York.

Additional polymers that can be included in wall 14 include a member selected from the group consisting of agar-agar acetate, acylated alginates, amylose triacetate, beta glucan acetate, beta glucan triacetate, acetyl alginate, triacetate of locust bean gum, alkanoyl carrageenan, acylated tragacanth, esterified gum karaya, cellulose derivatives substituted with an inorganic moiety such as a nitro group, semipermeable film forming materials as disclosed by Loeb and Sourirajan in U.S. Pat. No. 3,133,132, ionically associated semipermeable polyelectrolytes formed by the coprecipitation of a polycation and a polyanion as described in U.S. Pat. Nos. 3,173,876; 3,276,586; 3,541,005; 3,541,006; and 3,547,142; for example poly(styrene) derivatives such as poly(sodium styrene sulfonate) and poly(vinyltrimethyl ammonium chloride). These polymers and other polymers are known to the art and they are taught in *Handbook of Common Polymers*, by Scott and Roff, 1971 published by CRC Press, Cleveland, Ohio.

Materials suitable for forming wall 12 include a member selected from the group consisting of a microporous material and a hydrogel material. The microporous materials comprising wall 12 maintain their physical and chemical integrity during the period of time agent 17 is released from system 10. The microporous wall 12 can have preformed micropores, or the micropores of wall 12 can be formed when system 10 is in operation in the environment of use. A discussion of pore forming processes is presented later in this specification.

The microporous materials comprising wall 12 generally can be described as having a sponge-like appearance that provides a supporting structure for microscopic sized interconnected pores or voids. The materials can be isotropic wherein the structure is homogeneous throughout a cross-sectional area, the materials can be anisotropic wherein the structure is non-homogeneous throughout a cross-sectional area, or the materials can have both cross-sectional areas. The materials are opened-celled, as the micropores are continuous or connected, pores have an opening on both faces of the microporous wall. The micropores are interconnected through tortuous paths of regular and irregular shapes including curved, linear, curved-linear, randomly oriented continuous pores, hindered connected pores, and other interconnected porous paths discernible by microscopic examination.

Generally, the microporous walls are characterized as having a reduced bulk density as compared to the bulk density of the corresponding non-porous precursor microporous wall. The morphological structure of the total microporous wall have a greater proportion of total surface area than the non-porous wall. The microporous wall can further be characterized by the pore size, the number of pores, the tortuosity of the microporous paths, and the porosity which relates to the size and the number of pores. The pore size of a microporous wall is easily ascertained by measuring the observed pore diameter at the surface of the material under the electron microscope. Generally, materials possessing from 5% to 95% pores, and having a pore size of from 10 angstroms to 100 microns can be used for making wall 12. The pore size and other parameters characterizing the microporous wall can be obtained from flow measurements, where a liquid flux, J, is produced by a pressure difference, $\Delta P$, across a wall. The liquid flux through a wall with pores of substantially uniform radius extended through the wall and perpendicular to its surface with an area A is given by the relation A:

$$J = N\pi r^4 \Delta P / 8\eta \Delta x \quad (A)$$

wherein J is the volume transported per unit time through a wall area containing N number of pores of radius r, $\eta$ is the viscosity of the liquid, and $\Delta P$ is the pressure difference across the wall with thickness $\Delta x$. For this type of wall, the number of pores N can be calculated from relation B, wherein $\epsilon$ is the porosity defined as the ratio of void volume to the total volume of the wall:

$$N = \epsilon \cdot (A/\pi 2^2) \quad (B)$$

The pore radius then is calculated from relation C:

$$r = 8(J \cdot \Delta x \cdot \tau / \Delta P \cdot \epsilon)^{\frac{1}{2}} \quad (C)$$

wherein J is the volume flux through the wall per unit area produced by the pressure difference $\Delta P$ across the wall, $\eta$, $\epsilon$ and $\Delta x$ have the meaning defined above, and $\tau$ is the tortuosity defined as the ratio of the diffusional path length in the wall to the lamina thickness. Relations of the above type are discussed in *Transport Phenomena In Membranes*, by Lakshminatayaniah, N., Chapter 6, 1969, published by Academic Press, Inc., New York.

As discussed in the Lakshminatayania reference on page 336, in Table 6.13, the porosity of the wall having pore radii r can be expressed relative to the size of the transported molecule having a radius a, and as the ratio of molecular radius to pore size radius a/r is less than 0.3, the wall becomes substantially microporous as expressed by the osmotic reflection coefficient $\sigma$ which decreases below 0.5. Microporous walls with a reflection coefficient $\sigma$ in the range of less than 1, usually from 0 to 0.5, and preferrably less than 0.1 with respect to the active beneficial agent are suitable for manufacturing the systems. The reflection coefficient is determined by shaping the material in the form of a wall and carrying out water flux measurements as a function of hydrostatic pressure difference, and as a function of the osmotic pressure difference caused by the active agent. The osmotic pressure difference creates an osmotic volume flow, the hydrostatic pressure difference creates a hydrostatic volume flux, and the reflection coefficient is expressed by relation D:

$$\sigma = \frac{\text{hydrostatic pressure difference} \times \text{osmotic volume flux}}{\text{osmotic pressure difference} \times \text{hydrostatic volume flux}} \quad (D)$$

Properties of microporous materials are described in *Science*, Volume 170, pages 1302 to 1305, 1970; *Nature*, Volume 214, page 285, 1967; *Polymer Engineering and Science*, Volume 11, pages 284 to 388, 1971; U.S. Pat. Nos. 3,567,809 and 3,751,537; and in *Industrial Processing With Membranes*, by Lacey, R. E., and Loeb, Sidney, pages 131 to 134, 1972, published by Wiley, Interscience, New York.

Microporous materials are commercially available and they can be made by art-known methods. The materials can be made by etched nuclear tracking, by cooling a solution of flowable polymer below the freezing point whereby the solvent evaporates from the solution in the form of crystals dispersed in the polymer and then curing the polymer followed by removing the solvent crystals by cold stretching or hot stretching at low or high temperatures until pores are formed, by leaching from a polymer a soluble component by an appropriate solvent, by ion exchange reaction, and by polyelectrolyte processes. In a presently preferred embodiment, the microporous wall is formed in the environment of use from a precursor microporous wall. This latter wall contains a poreformer that is removed from the precursor by dissolving or leaching therefrom, forming an operable microporous wall. The pore-formers useful for the present purpose are a member selected from the group consisting of about 1 to 50% by weight of a solid pore-former, about 0.5 to 20% by weight of a liquid pore-former, and mixtures thereof. Examples of pore-formers are presented later in the specification. In another embodiment, the microporous wall can be formed by a compression coating technique. In this latter embodiment, a rigid microporous wall substantially free of substances soluble or swellable in the fluid present in the environment of use can be formed by compression coating a microporous material around the exterior, perimeter of the system. Generally, the microporous wall is formed under a compression pressure of 500 to 5000 kg/cm$^2$, usually in a rotary machine. Processes for preparing microporous walls are described in *Synthetic Polymer Membranes*, by R. E. Kesting, Chapters 4 and 5, 1971, published by McGraw-Hill, Inc.; *Chemical Reviews, Ultrafilter Membranes and Ultrafiltration*, Volume 18, pages; 373 to 455, 1934; *Polymer Engineering and Science*, Volume 11, No. 4, pages 284 to 288, 1971; *J. Appl. Poly. Sci.*, Volume 15, pages 811 to 829, 1971; in U.S. Pat. Nos. 3,565,259; 3,615,024; 3,751,536; 3,801,692; 3,852,224; 3,849,528; and, 3,929,509; and in Great Britain Pat. No. 1,459,356.

Microporous materials suitable for making distant wall 12 include microporous polycarbonates comprising linear polyesters of carbonic acid in which carbonate groups recur in the polymer chain by phosgenation of a dihydroxy aromatic such as bisphenol, microporous poly(vinylchloride), microporous polyamides such as polyhexamethylene adipamide, microporous modacrylic copolymers including those formed of polyvinyl chloride and acrylonitrile, styrene-acrylic acid copolymers, microporous polysulfones, characterized by diphenylene sulfone groups in the linear chain thereof, halogenated polymers such as polyvinylidene fluoride, polyvinylfluoride and polyfluorohalocarbon, polychloroethers, cellulose esters, cellulose ethers, cellulose acylates, acetal polymers such as polyformaldehyde, polyesters prepared by esterification of a dicarboxylic acid or anhydride with a polyol, poly(alkylenesulfides), phenolic polyesters, microporous poly(saccharides) having substituted and unsubstituted anhydroglucose units, asymmetric porous polymers, cross-linked olefin polymers, hydrophobic and hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,061; 3,852,224; 3,852,388; 3,853,631; and 3,948,254; in British Pat. No. 1,126,849, and in *Chem. Abst.*, Volume 71, 4274F, 22572F, and 22573F, 1969.

Additional microporous materials include materials that are substantially insoluble in the fluid present in the environment of use, are inert, non-disintegrating, non-eroding and are materials that can be compressed in powder form, applied by air suspension, dipping techniques, and the like. Exemplary materials include poly(urethanes), copolymers of divinyl chloride and acrylonitrile, inorganic materials such as dicalcium phosphate dihydrate, tricalcium phosphate and anhydrous calcium sulphate, cross-linked chain-extended poly(urethanes), microporous poly(urethanes) in U.S. Pat. No. 3,524,753, poly(imides), poly(benzimidazoles), collodion (cellulose nitrate with 11% nitrogen), regenerated proteins, microporous materials prepared by diffusion of multivalent cations into polyelectrolyte sols as in U.S. Pat. No. 3,565,259, anisotropic microporous materials of ionically associated polyelectrolytes, microporous polymers formed by the coprecipitation of a polycation and a polyanion as described in U.S. Pat. Nos. 3,276,589; 3,541,006; and 3,546,142, derivatives of poly(styrene) such as poly(sodium styrene sulfonate) and poly(vinylbenzyltrimethyl-ammonium chloride), the microporous materials disclosed in U.S. Pat. Nos. 3,615,024; 3,646,178; and 3,852,224; the microporous walls having a plurality of micropores with diffusional conduits through the wall as in U.S. Pat. No. 3,948,254, and the like. In a presently preferred embodiment, the reflection coefficient for the microporous wall to the pore former can have a range of 0 to 0.79.

Hydrogel materials useful for the present purpose include hydrogels that maintain their physical and chemical integrity in the environment of use and during the time beneficial agent is dispensed from the system. The hydrogels useful for forming outer wall 12 broadly include lightly cross-linked hydrophilic polymers. These polymers can have cross-links formed by covalent or ionic bonds. The hydrogels permit the passage of fluids and solutions, and they swell in the presence of fluid to a high degree without dissolution, usually exhibiting a 5 to 50 fold volume increase. The swelling of the hydrogels imparts a softness and gentle cushion response to touch in system 10. These properties enhance the usefulness of hydrogels for forming outer wall 12 of system 10 as they increase the receptibility of system 10 for use in a body. The hydrogels useful for this invention include those that are non-toxic and non-irritating in biological environments.

Exemplary hydrogels include poly(hydroxyalkyl methacrylates), poly(acrylamide), poly(methacrylamide), poly(N-vinyl-2-pyrrolidone), anionic and cationic hydrogels, polyelectrolyte complexes, poly(vinyl alcohol) having a low acetate residual and cross-linked with glyoxal, formaldehyde or glutaraldehyde, methylcellulose cross-linked with a dialdehyde, a cross-linked mixture of agar and sodium carboxymethylcellulose, a water-insoluble, water-swellable copolymer produced by forming a dispersion of finely divided copolymers of maleic anhydride with styrene, ethylene, propylene, butylene or isobutylene cross-linked with from about 0.001 to about 0.5 moles of a polyunsaturated cross-linking agent per mole of maleic anhydride in the copolymer as disclosed in U.S. Pat. No. 3,989,586, water-swellable polymers of N-vinyl lactams as disclosed in U.S. Pat. No. 3,992,562, semi-solid, crosslinked poly(vinyl pyrrolidone), cross-linked gelatin, cross-linked poly(acrylamide), diester cross-linked polyglucan hydrogels as described in U.S. Pat. No. 4,002,173, anionic hydrogels of heterocyclic N-vinyl monomers as described in U.S. Pat. No. 4,036,788, ionogenic hydrophilic gels as described in *J. Biomedical Mater. Res.*, Volume 7, pages 123 to 136, 1973, and the like.

As used herein, the expression "pore-former" includes pore-forming solids and pore-forming liquids. In the latter expression, the term liquid for this invention generically embraces semi-solids and viscous fluids. The pore-formers can be inorgenic or organic. The term pore-former for both solids and liquids includes substances that can be dissolved, extracted or leached from the microporous precursor wall by fluid present in the environment of use to form an operable, open-celled type microporous wall. Additionally, the pore-formers suitable for the invention include pore-formers that can be dissolved, leached or extracted without causing physical or chemical changes in the polymer. The pore-forming solids have a size of about 0.1 to 200 microns and they include alkali metal salts such as lithium carbonate, sodium chloride, sodium bromide, sodium carbonate, potassium chloride, potassium sulfate, potassium phosphate, sodium benzoate, sodium acetate, sodium citrate, potassium nitrate, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including the sugars sucrose, glucose, fructose, mannitol, mannose, galactose, aldohexose, altrose, talose, sorbitol, and the like. Organic aliphatic oils including diols and polyols, aromatic oils including diols and polyols, and other polyols such as polyhydric alcohol, polyalkylene glycol, polyglycol, poly($\alpha,\omega$)-alkylenediols, and the like. The pore-formers are non-toxic and on their removal from wall 12, channels are formed through wall 12 that fill with fluid. The channels become a means, or diffusional path from diffusion of agent and solution from the distribution zone through the liquid in the liquid-filled pores. The pores extend from inside wall 12 to the outside of wall 12 for effective release of agent to the exterior of the system. In a preferred embodiment, non-toxic pore forming agents selected from the group consisting of inorganic salts, organic salts and carbohydrates, are used when system 10 is made for use in a biological environment.

Distribution zone 13 positioned between wall 12 and wall 14 comprises a layer of a member selected from the group consisting of organic and inorganic compounds. The compounds, in either embodiment, are soluble in fluid that enters zone 13 from the exterior of system 10, thereby forming a solution that is released to the exterior through the microporous paths in wall 12. Representative inorganic compounds that can be used for forming zone 13 include magnesium chloride, sodium chloride, lithium chloride, potassium chloride, sodium carbonate, potassium carbonate, manganese carbonate, sodium sulfite, potassium sulfite, lithium sulfite, magnesium sulfate, calcium bicarbonate, sodium bicarbonate, potassium bicarbonate, sodium sulfite, potassium sulfite, lithium sulfite, magnesium sulfite, potassium acid phosphate, sodium acid phosphate, and the like. Typical organic compounds include carbohydrates such as glucose, sucrose, fructose, raffinose and lactose, and other organic compounds soluble in water and biological fluids such as mannitol, inositol, urea, magnesium succinate, tartaric acid, and the like.

Figure 8:
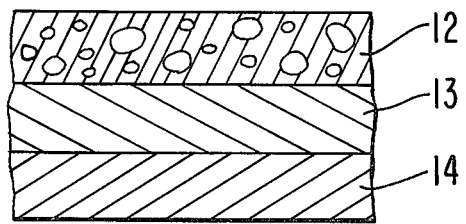
FIG. 8 depicts a cross-section of an osmotic system made according to the invention, illustrating a layered arrangement of the initial structure of an osmotic system.

The manufacture of zone 13 between wall 12 and wall 14 produces optionally in another embodiment a laminate. The laminate can be described as initially consisting essentially of three lamina or layers. These are, as depicted in FIG. 8, lamina 12, which is synonymous with microporous wall 12, lamina 13 which synonymous with layer 13, and during the operation of system 10 results in fluid distribution zone 13, and lamina 14, which is synonymous with semipermeable wall 14.

The expression "flux regulator" and "flux regulating agent" as used herein means a compound, polymer or the like, when added to microporous wall 12, or semipermeable wall 14, assists in regulating the fluid permeability or liquid flux through walls 12 and 14. The agent can be preselected to increase the liquid flow, a flux enhancer, or decrease liquid flow, a flux decreaser. Agents that produce a marked increase in permeability to fluid such as water, are often hydrophilic, while those that produce a decrease in fluids such as water, are essentially hydrophobic. The flux regulators, in some embodiments, can increase the flexibility and workability of walls 12 and 14. The flux enhancers, in one presently preferred embodiment, are polyhydric alcohols and derivatives thereof, such as polyalkylene glycols of the formula H—O—alkylene)$_n$OH, wherein the bivalent alkylene radical is straight or branched chain and has from 1 to 10 carbon atoms, and n is 1 to 500, or higher. Typical glycols include polyethylene glycol 300, 400, 600, 1500, 1540, 4000 and 6000, of the formula H—OCH$_2$CH$_2$)$_n$OH, wherein n is respectively 5 to 5.7, 8.2 to 9.1, 12.5 to 13.9, 29 to 36, 29.8 to 37, 68 to 84, and 158 to 204. Other polyglycols include low molecular weight glycols such as polypropylene glycol, polybutylene glycol, and polyamylene glycol. Typical hydrophobic regulators include esters of rosin and hydrogenated esters of rosin, such as glyceryl esters of hydrogenated rosin, glyceryl esters of partially hydrogenated rosin, and the like. The flux regulators are known to the art in U.S. Pat. No. 4,077,407.

The expressions "active agent" and "beneficial agent" as used herein broadly include any compound, composition of matter, or mixture thereof, that can be delivered from system 10 to produce a beneficial and useful result. The agent can be soluble in a fluid that enters compartment 16 and functions as its own osmotically effective solute, or it can have limited solubility in the fluid and be mixed with an osmotically effective compound, or osmagent, that is soluble in the fluid. The active agents include air purifiers, algicides, antioxidants, biocides, catalysts, chemical reactants, cosmetics, contraceptives, drugs, disinfectants, food supplements, fermentation agents, fertility inhibitors, fertility promoters, fungicides, germicides, herbicides, insecticides, micro-organism attenuators, pheremones, pro-drugs, plant growth inhibitors, pesticides, preservatives, rodenticides, sex sterilants, slimicides, vitamins and other agents that benefit the environment of use and mankind.

In the specification and the accompanying claims, the term drug includes any physiologically or pharmacologically active substance that produces a localized or a systemic effect or effects in animals, avians, reptiles and fish. The term animal as used herein includes mammals, humans, primates, domestic household, sport or farm animals, such as sheep, goats, cattle, horses, dogs, cats and pigs, for administering to laboratory animals such as mice, rats and guinea pigs, and to zoo animals. The active drugs that can be delivered include inorganic and organic drugs that act on the central nervous system, psychic energizers, tranquilizers, anticonvulsants, muscle relaxants, antiparkinson, analgesic, anti-inflammatory, anesthetic, antispasmodic, muscle contractants, anti-microbials, anti-malarials, hormonal agents, sympathomimetic; cardiovascular, diurectics, antiparasitic, neoplastics, hypoglycemic, essential amino acids, eye drugs, electrolytes and the like. The beneficial drugs are known to the art in Remington's *Pharmaceutical Sciences,* 14th Edition, 1970, published by Mack Publishing Company, Easton, Pa.; and in *The Pharmacological Basis of Therapeutics,* by Goodman and Gilman, 4th Edition, 1970, published by the MacMillian Company, London.

Representative of typical drugs that can be dispensed in the vagina for a system sized, shaped and adapted for easy insertion and comfortable retention in the vagina include allantorn, aminoacridine hydrochloride, benzocaine, benzalkonium chloride, candicidin, dienestrol, dibucaine, ephedrine sulfate, furazolidone, gentain violet, hydrocortisone, methylbenzethium chloride, phenylmercuric acetate, providone-iodine, sulfanilamide, sulfisoxazole, tetracaine, undecylenate, and the like. See *Techniques of Medication,* by Eric W. Martin, pages 106 to 107, 1969, published by J. B. Lippincott Company, Philadelphia.

Representative of drugs that can be dispensed in the ano-rectal environment from a system shaped, sized and adapted for easy insertion and comfortable placement therein include acetarsol, adrenaline with benzocaine, aminophylline, aminophylline with pentobarbital sodium, ampicillin, aspirin, astroscopolamine, belladonna, benzocaine, bisacodyl, bismuth subgallate, caffeine, ergotamine tartrate, chloralhydrate, chlorpromazine, cinchocaine, cyclomethycaine sulfate, dimenhydrinate, hydrocortisone, ichthammol, indomethacin, isoprenaline, metronidazole, morphine, oxymorphine hydrodiamine, thiethylperazine maleate, and the like. See *Martindale The Extra Pharmacopolia,* Edited by Ainley Wade, *General Index,* page 2056, 1977, published by the Pharmaceutical Press, London; and, *National Drug Code Directory,* published by Public Health Service, U.S. Department of Health, Education and Welfare, Washington.

The drug present in the reservoir of the osmotic system can be in various forms, such as uncharged molecules, molecular complexes, prodrug, pharmacologically acceptable salts such a hydrochlorides, hydrobromides, sulfate, laurylate, palmitate, phosphate, nitrate, borate, acetate, maleate, tartrate, oleate, and salicylate. For acidic drugs, salts of metals, amines, or organic cations, for example quaternary ammonium salts can be used. Derivatives of drugs such as esters, ethers and amides, which have solubility characteristics suitable for use herein, can be used alone, or mixed with an osmotically effective compound. Also, a drug that is water insoluble can be used in a form that is a water soluble derivative thereof to effectively serve as a solute, and on its release from system 10, is converted by enzyme, hydrolyzed by body pH, or other metabolic processes to the original form, or to a biologically active form. The agent can be present in the reservoir as a suspension, dispersion, paste, cream, particle, granule, emulsion, solution, powder, and the like. Also, the agent can be mixed with a binder, dispersant, emulsifier, wetting agent or dye.

The amount of agent present in system 10 is preferably in excess of the amount that can be dissolved in the fluid that enters reservoir 16. Under this physical state, when agent 17 is in excess, system 10 will osmotically operate to give a substantially constant rate of release over time. The rate of agent release can also be varied by having different amounts of agent in the reservoir to form solutions containing different concentrations of agent for delivery from the device 10. Generally, osmotic device 10 can house from 0.01 ng to 7 g or more, with individual devices containing for example, 25 ng, 1 mg, 5 mg, 250 mg, 500 mg, 1 g, 1.5 g, 5 g, 7.5 g, 10 g, and the like.

The osmotically effective compound that can be used for the purpose of the invention includes organic and inorganic compounds or solutes that exhibit an osmotic pressure gradient across semipermeable wall 14 against fluid present in distribution zone 13. The osmotically effective compounds are used mixed with an agent that has limited solubility in the external fluid with the compound forming a saturated solution containing agent that is osmotically delivered through passageway 15 into distribution zone 13. Osmotically effective compounds useful for the present purpose include magnesium sulfate, magnesium chloride, sodium chloride, lithium chloride, potassium sulfate, sodium carbonate, potassium acid phosphate, mannitol, urea, sucrose and the like. The osmotically effective compounds are also known as osmagents and they are disclosed in U.S. Pat. Nos. 3,845,770 and 4,077,407. These patents are assigned to the ALZA Corporation of Pala Alto, Calif.

The expression passageway as used herein for passageway 15 comprises means and methods suitable for relasing agent 17 into distribution zone 13 include an aperture, orifice or bore through semipermeable wall 14 formed by mechanical procedures, laser drilling, or eroding an erodible element such as a gelatine plug during operation of osmotic system 10. A detailed description of osmotic passageways and the maximum and minimum dimensions for a passageway are disclosed in U.S. Pat. Nos. 3,854,770 and 3,916,899. These patents are assigned to the ALZA Corporation of Pala Alto, Calif.

Osmotic system 10 of this invention are manufactured by standard techniques. For example, in one embodiment, agent 17 and other ingredients that may be housed in compartment 16 and a solvent are mixed into a solid, semisolid, or gel formed by ballmilling, calendaring, stirring or rodmilling and then pressing it into a preselected shape. Semipermeable wall 14 then is applied by molding, spraying or dipping the pressed shape into a semipermeable wall forming material, or in another embodiment, wall 14 can be cast into a film, shaped to the desired dimensions, partially sealed to define a hollow compartment that is filled with agent and then closed. Device 10 also can be manufactured with an empty compartment that is filled through the passageway. High frequency electronic techniques can be used to provide devices with a wall having clean edges. Another, and presently preferred technique that can be used is the air suspension procedure. This procedure consists in suspending and tumbling the pressed agent in a current of air and wall forming material until the wall is applied to the agent. The air suspension procedure is described in U.S. Pat. No. 2,779,241; *J. Am. Pharm Assoc.,* Volume 48, pages 451 to 459, 1959; and ibid, Volume 49, pages 82 to 84, 1960.

Layer 13, which on dissolution and passage from system 10 becomes distribution zone 13, can be applied to the surface of wall 14 distant from compartment 16, that is the exterior surface of wall 14, by different manufacturing procedures. For example, the inorganic, or the organic compound can be mixed with gelatine and water followed by dipping semipermeable wall 14 surrounding compartment 16 into the gelatine compound solution. This procedure deposits a layer on the exterior of wall 14, followed by permitting the layer to dry to hardness. Another procedure consists in placing semipermeable wall 14 surrounding compartment 16 in a mold, and then filling the space between the inside surface of the mold and the exterior of wall 14 with the compound. Next, the mold can be frozen, or pressure can be applied to fix layer 13 into the exterior of wall 14. Layer 13 can be also applied by the air suspension techniques as described above. Microporous wall 12 in a preferred embodiment is formed by the air suspension technique. Other standard manufacturing procedures are described in *Modern Plastic Encyclopedia,* Volume 46, pages 62 to 70, 1969, published by McGraw Hill, Inc.; and in *Pharmaceutical Sciences,* by Remington, Fourteenth Edition, pages 1626 to 1678, 1970, published by the Mack Publishing Company.

The following examples are merely illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An osmotic therapeutic system for the controlled and continuous oral release of the beneficial drug potassium chloride was made as follows: (a) first, 5 kgs consisting of 750 mgs of potassium chloride drug cores were compressed in a Manestry machine with a 7/16 inch punch under a pressure head of 1-½ tons to form a precompartment having an area of 3.12 cm². Then, (b) 318 g of cellulose acetate having an acetyl content of 32% was homogeneously blended with 36 g of polyethylene glycol 400, which glycol acts as a flux enhancer, and also increases the workability of the materials, and the blend added to 7060 g of solvent. The solvent consisted of acetone:water, in the ratio of 88.5:11.5, wt:wt. The solvent and the ingredients were blended in a high shear blender for 25 to 30 minutes to yield an approximate 5% cellulose acetate polymer solution. The blending was carried out at room temperature and atmospheric pressure.

Next, (c) the semipermeable wall forming composition prepared in (b) and the precompartment prepared in (a) were placed in an Accela coater and uniformly coated with a semipermeable wall. Finally, the coated compartments were dried in an air oven at 50° C. for one week. The semipermeable, cellulose acetate wall surrounding the drug was 5 mil thick. An 8.3 mil aperture was laser drilled through the semipermeable wall. Then, (d), layer 13 was formed and intimately applied onto the exterior surface of the semipermeable wall formed in (c) as follows: 100 g of potassium chloride, 18 g of poly(vinylpyrrolidone), and 1200 ml of water were blended and coated onto the semipermeable wall by air suspension. After air drying in a warm oven, the layer had a thickness of 2.5 mils.

Finally, (e), a microporous wall was formed and coated onto the osmotic system as follows: to 65 g of cellulose acetate having an acetyl content of 32% was added 41 g of pore-forming sorbitol, 11.7 g of polyethylene glycol 400, and a solvent consisting of 1900 ml of acetone and 375 ml of water. All the ingredients were thoroughly blended in a high shear blender for 25 minutes. Next, the osmotic system, as prepared in a-d, and the microporous wall forming composition, as prepared in e, were placed in the air suspension machine and air tumbled until a 4.7 mil thick microporous wall was applied to the osmotic system.

Figure 9:
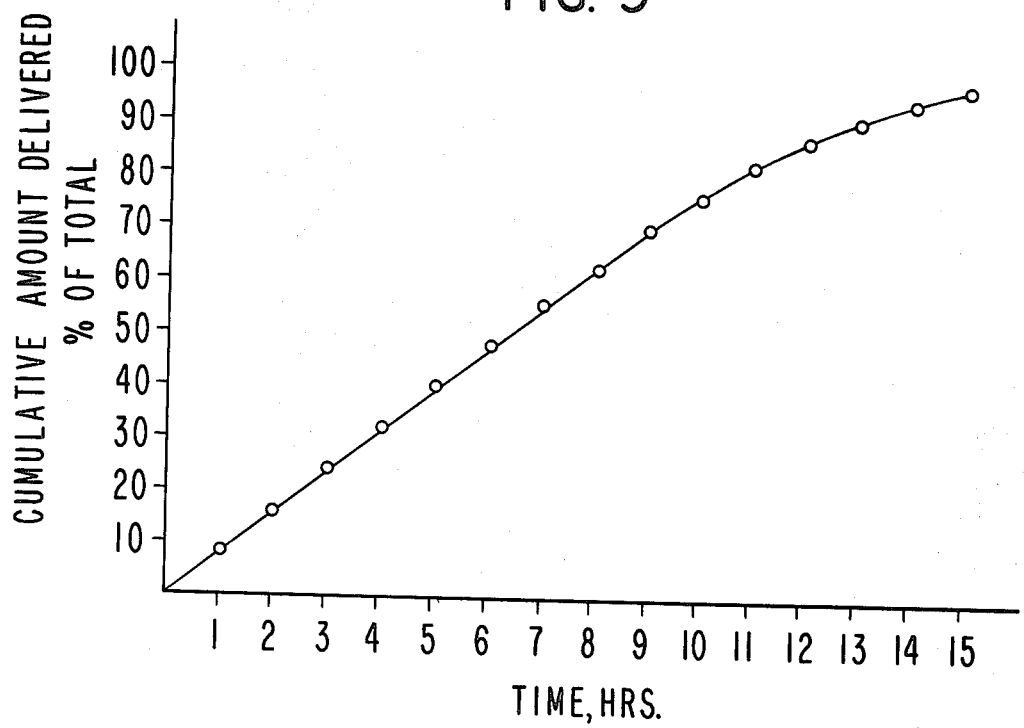
FIGS. 9, 11 and 13 are graphs that show the cumulative amount of drug delivered over a total time period; and, FIGS. 10, 12 and 14 show graphs that depict the average rate of release per hour for osmotic systems made according to the invention.
Figure 10:
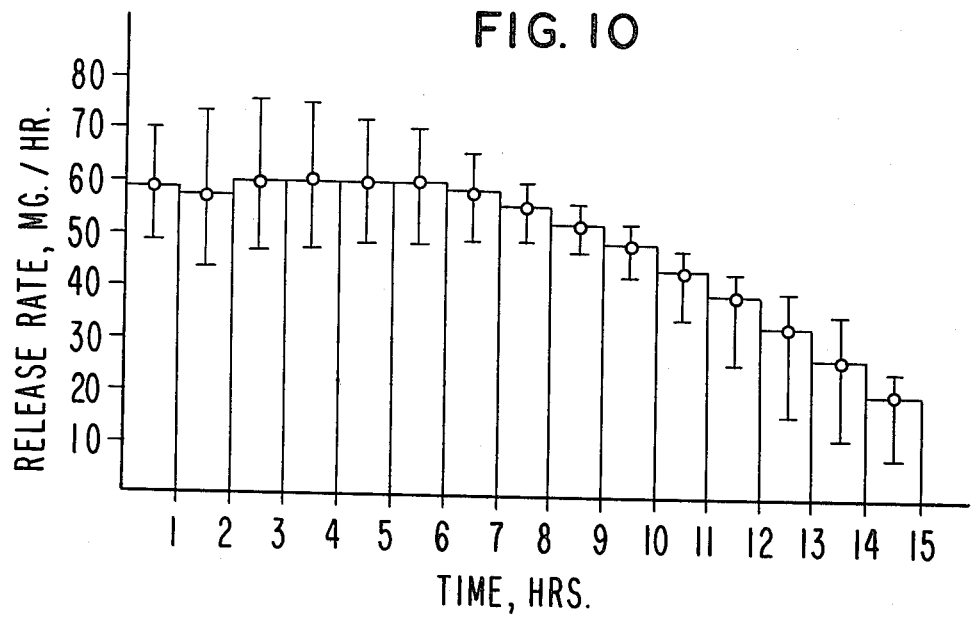

The osmotic systems have an average rate of release of 60 mgs/hr for potassium chloride. Accompanying FIG. 9 shows the cumulative amount of potassium chloride delivered over a total time period for an osmotic system prepared according to this example. Accompanying FIG. 10 shows the average release rate in mgs/hr for eight osmotic systems prepared according to this example.

EXAMPLE 2

The general procedure of Example 1 was repeated with the following conditions: the precompartment consisted of 187 mgs of potassium chloride and 1 mg of magnesium stearate. A ¼ inch punch was used and the area was 1.12 cm². The semipermeable wall was formed from cellulose acetate having an acetyl content of 32%, with 401 g mixed in acetone-water solvent consisting of 8560 ml of acetone and 875 ml of water. The semipermeable wall was 3.4 mils thick and the diameter of the passageway was 5 mils. The layer coated on the exterior of the semipermeable wall was 2.5 mils thick and it was coated thereon from a composition consisting essentially of 132 g of potassium chloride and 33 g of poly(vinylpyrrolidone) in 2000 g water. The microporous wall was formed from a composition consisting essentially of 103 g of cellulose acetate having an acetyl content of 32% and 85 g sorbitol in a solvent consisting of 3050 ml of acetone and 600 ml of H₂O. The microporous wall was 4 ml thick.

Figure 11:
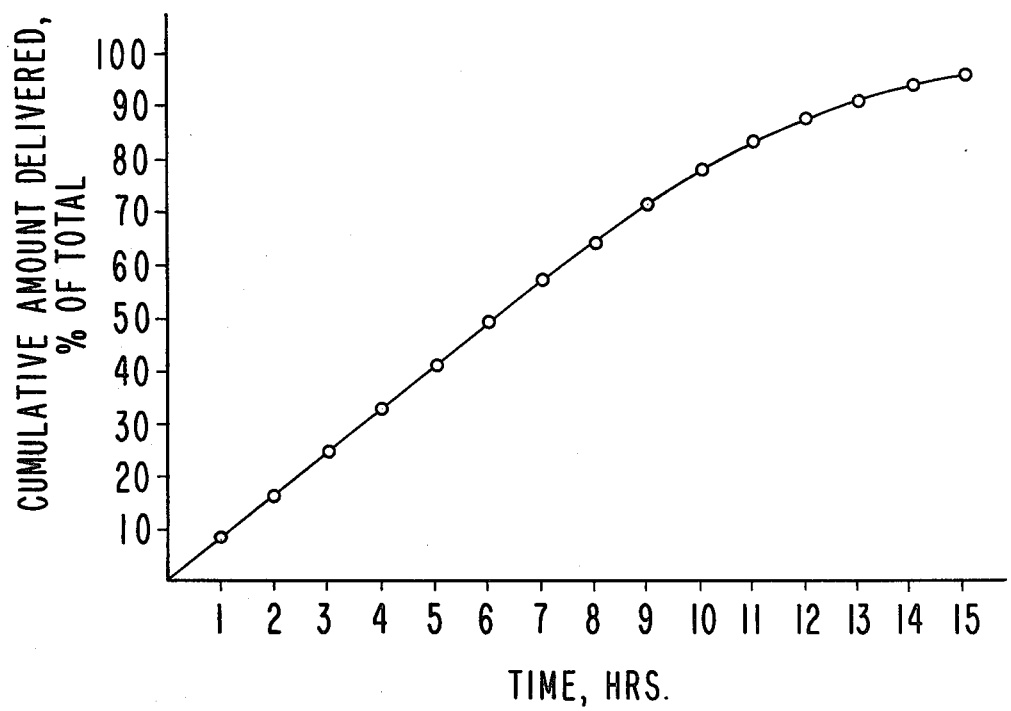
Figure 12:
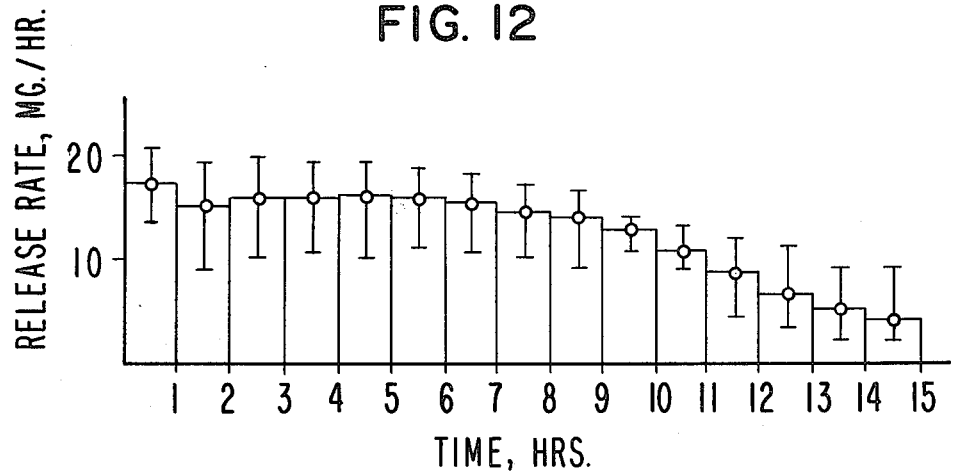

The osmotic systems prepared according to this example had an average rate of release of 15 mg/hr of potassium chloride over time. Accompanying FIG. 11 shows the cumulative amount of potassium chloride delivered by an osmotic system over a 15 hr period. Accompanying FIG. 12 shows the average rate of release for 10 osmotic systems.

EXAMPLE 3

The procedure of Example 1 was followed in this example. The parameters of the osmotic systems of this example are as follows: the precompartment consisted of 375 mg of potassium chloride and 2 mg of magnesium stearate. A ⅜ inch punch was used and the area was 1.75 cm². The semipermeable wall was formed from a composition comprising 396 g of cellulose acetate having an acetyl content of 32% and 44 g of polyethylene glycol 400, applied from a solvent consisting of 9416 ml of acetone and 916 ml of water. The semipermeable wall was 6 mils thick and the passageway had a diameter of 8 mils. The layer formed on the exterior surface of the semipermeable wall was 2.5 mils thick, and it consisted of 110 g of potassium chloride and 19 g of poly(vinylpyrrolidone) applied from 1900 ml of water. The microporous wall was formed from a composition consisting essentially of 96 g of cellulose acetate having an acetyl content of 32%, 17.5 g of polyethylene glycol 400 and 61.2 g of sorbitol in 3050 ml of acetone and 600 ml of water. The microporous wall was 4.8 mils thick.

Figure 13:
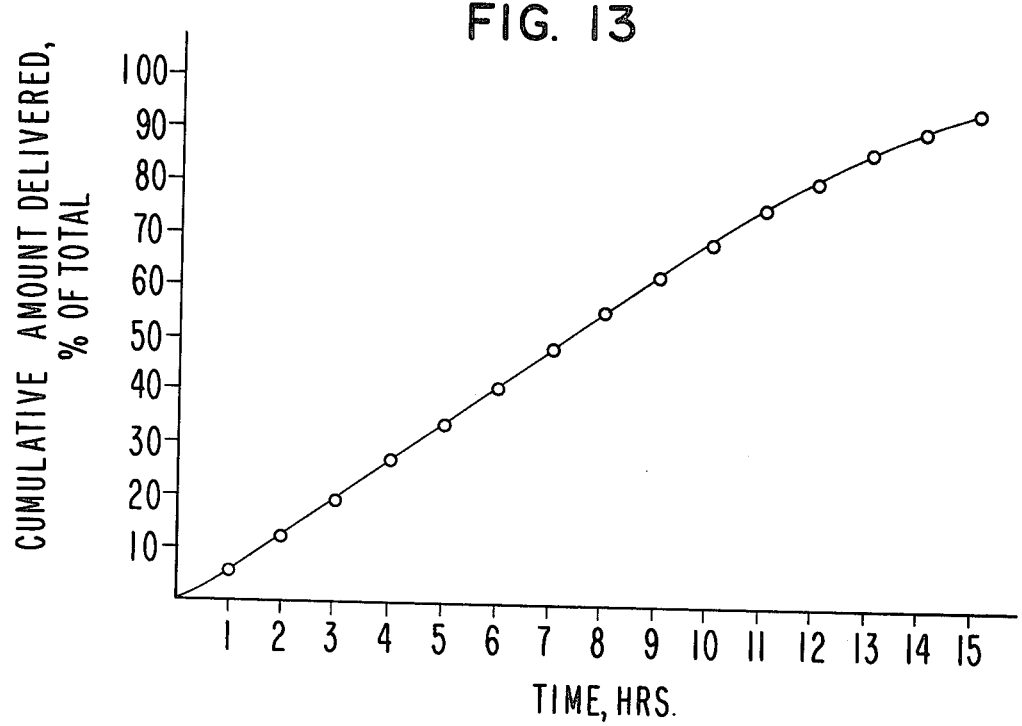
Figure 14:
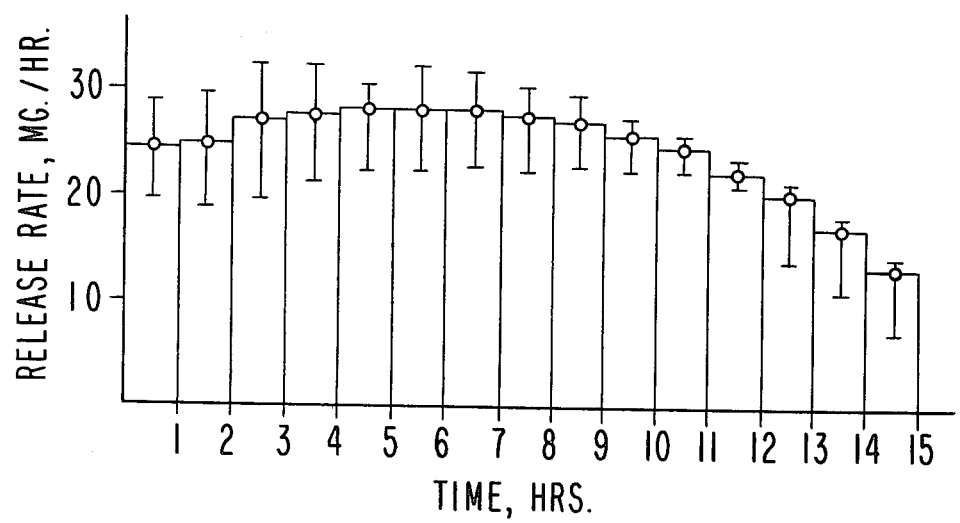

The osmotic systems prepared according to this example had an average rate of release of 28 mg per hour. Accompanying FIG. 13 shows the cumulative amount of potassium chloride delivered by an osmotic system prepared according to this example. FIG. 14 shows the average rate of release for 10 systems manufactured according to this example.

EXAMPLE 4

Osmotic therapeutic system designed as a suppository, sized, shaped and adapted for dispensing drug in the ano-rectal environment is manufactured as follows: first, a conical shaped, stainless steel mold provided with a base portion, a tapered longitudinally extended body portion, and a rounded lead portion, is filled through an opening in the base with a composition comprising 750 mg of 8-[(dimethylamino)methyl]-7-methoxy-3-methyl-2-phenyl-4H-benzopyran-4-one hydrochloride and 2 mg of magnesium stearate and the composition is removed from the mold and surrounded with a semipermeable wall supplied by air suspension. An aperture is laser drilled through the semipermeable wall at the lead portion. Then, a layer of sucrose is coated onto the exterior surface of the semipermeable wall, and after drying, a non-erodible polymeric microporous wall having a pore-former therein, is air suspension laminated onto the free surface of the layer. The system, when placed in the environment of use, releases an effective amount of drug at a controlled rate over time.

EXAMPLE 5

A drug reservoir consisting essentially of theophylline sodium glycinate was prepared by mixing 2 kg of the drug with 100 g of polyvinyl pyrrolidone, which was converted to wet granules by mixing the glycinate-pyrrolidone with ethanol:water, (95.5% by volume, 450 ml). The wet granules were passed through a No. 40 sieve and dried in an oven at 50° C. for 8 hrs. After drying, the granules were passed through a No. 30 mesh sieve. Then 20 g of magnesium stearate was passed through a No. 40 sieve and mixed with the granules, with the drug reservoir formed by compressing with a Manesty machine using a 7/16 inch punch to yield a reservoir 3 cm$^2$ area.

A semipermeable wall was formed by blending 11.05 g of hydroxypropyl methanol, 62.05 g of cellulose acetate having an acetyl content of 32% and 8.50 g of polyethylene glycole-400, admixed with a solvent consisting of 1700 ml of methylene chloride and 700 ml of methanol, for 45 minutes at high shear. The drug reservoirs, consisting of 600 mg of theophylline sodium glycinate, were coated with the semipermeable wall forming composition by air suspension in a Wurster coater. The coated reservoirs were dried for 24 hours at 50° C., and a 10 ml passageway laser drilled through the semipermeable wall.

Next, a zone of distribution was prepared by coating the above with a coat consisting of 170 g of sorbitol, 67 of polyvinyl pyrrolidone and 300 ml of water.

The microporous forming wall was prepared by (a) dissolving 55 g of cellulose acetate having an acetyl content of 38.3 on 870 ml of methylene chloride and 500 ml of methanol, and (b) dissolving 45 g of sorbitol in 414 ml of methanol and 57 ml of water and then mixing (a) and (b) together at high shear. The microporous wall was applied by air suspension. The system releases 15 mg/hr of theophylline.

While the invention has been illustrated and described in detail, it is not intended to be limited to the details disclosed, since various modifications and changes may be made without departing in any way from the spirit of the inventor.

We claim:

1. A process for manufacturing a drug delivery device, which process comprises the steps of:
   (a) pressing a drug formulation into a shaped, solid mass;
   (b) coating the mass with a composition comprising a semipermeable polymer permeable to the passage of fluid and impermeable to the passage of drug to form a semipermeable wall surrounding a compartment housing the formulation;
   (c) drilling an outlet passageway in the semipermeable wall of a predetermined size for osmotically pumping the formulation through the passageway;
   (d) coating the semipermeable wall with a layer of a member soluble in fluid that enters the device and is selected from the group consisting of a salt, a carbohydrate, and mixtures thereof, which layer separates the semipermeable wall from a microporous wall, said microporous wall formed by;
   (e) coating the layer with a composition comprising a microporous polymer to form a microporous wall surrounding the layer, thereby forming the device.

2. The process for manufacturing the drug delivery device of claim 1 wherein the device is shaped, sized and adapted for delivering the drug formulation in an ano-rectal canal.

3. The process for manufacturing the drug delivery device of claim 1 wherein the device is shaped, sized and adapted for delivering the drug formulation in a vagina.

4. The process for manufacturing the drug delivery device of claim 1 wherein the device is shaped, sized and adapted for delivering the drug formulation in a gastrointestinal tract.

5. The process for manufacturing the drug delivery device of claim 1 wherein the semipermeable wall is coated with a layer of salt by dipping the wall into a salt solution.

6. The process for manufacturing the drug delivery device of claim 1 wherein the coating process for forming the walls and the layer is an air suspension coating process.

7. The process for manufacturing the drug delivery device of claim 1 wherein the coating process for forming the walls and the layer uses a member selected from the group consisting of organic and inorganic solvents, and mixtures thereof.

8. The process for manufacturing the drug delivery device of claim 1 wherein the composition comprising the microporous polymer has a pore-forming agent mixed therein.

9. A process for manufacturing a drug delivery device which process comprises the steps of:
   (a) pressing a drug formulation into a shaped, solid mass;
   (b) coating the mass with a composition comprising a semipermeable polymer permeable to the passage of fluid and impermeable to the passage of drug to form a semipermeable wall that surrounds a compartment housing the formulation;
   (c) drilling an outlet passageway in the semipermeable wall of a predetermined size for osmotically pumping the formulation through the passageway;
   (d) coating the semipermeable wall with a layer of a member soluble in fluid that enters the device and is selected from the group consisting of a salt, a carbohydrate and mixtures thereof, which layer separates the semipermeable wall from a hydrogel wall, said latter wall formed by;
   (e) coating the layer with a hydrogel to form a hydrogel wall surrounding the layer, thereby forming the device.

10. The process for manufacturing the drug delivery device of claim 9 wherein the device is shaped, sized and adapted for delivering the drug formulation in an ano-rectal canal.

11. The process for manufacturing the drug delivery device of claim 9 wherein the device is shaped, sized and adapted for delivering the drug formulations in a vagina.

12. The process for manufacturing the drug delivery device of claim 9 wherein the device is shaped, sized and adapted for delivering the drug formulation in a gastrointestinal tract.

13. The process for manufacturing the drug delivery device of claim 9 wherein semipermeable wall is coated with a layer of salt by dipping the wall into a salt solution.

14. The process for manufacturing the drug delivery device of claim 9 wherein the coating process for forming the walls and the layer is an air suspension coating process.

15. The process for manufacturing the drug delivery device of claim 9 wherein the coating process for forming the walls and the layer uses a member selected from the group consisting of organic and inorganic solvents, and mixtures thereof.

* * * * *